United States Patent [19]

Bickelhaupt et al.

[11] Patent Number: 4,874,897
[45] Date of Patent: Oct. 17, 1989

[54] BISPHOSPHINE PRODUCTION

[75] Inventors: Friedrich Bickelhaupt; Thomas van der Does, both of Amsterdam, Netherlands

[73] Assignee: Shell Oil Company, Houston, Tex.

[21] Appl. No.: 190,187

[22] Filed: May 4, 1988

[30] Foreign Application Priority Data

May 5, 1987 [NL] Netherlands .......................... 8701058

[51] Int. Cl.$^4$ ............................................... C07F 9/02
[52] U.S. Cl. ............................................ 568/13; 568/8
[58] Field of Search ................................ 568/13, 17, 8

[56] References Cited

U.S. PATENT DOCUMENTS 3,036,132 5/1962 Belker ..................................... 568/17
3,382,173 5/1968 Zorn et al. ............................. 568/17

Primary Examiner—John Doll
Assistant Examiner—Short L. Hendrickson
Attorney, Agent, or Firm—Dean F. Vance

[57] ABSTRACT

Bis[di(alkoxyphenyl)phosphino]alkanes are produced by reacting an alkoxyphenyl Grignard with phosphorus trichloride and converting the resulting di(alkoxyphenyl)phosphorus chloride to the corresponding phosphine. The di(alkoxyphenyl)phosphine is reacted with a dihaloalkane to produce the desired bisphosphine.

7 Claims, No Drawings

BISPHOSPHINE PRODUCTIONg

FIELD OF THE INVENTION

This invention relates to the production of bis[di(alkoxyaryl)phosphino]alkanes, and aparticularly to the production of 1,3-bis[di(2-alkoxyphenyl)phosphino]-propane.

BACKGROUND OF THE INVENTION

In contrast with the production of substituted phosphines wherein the substituents are aliphatic, the production of phosphines having aromatic substituents is frequently very difficult, depending on the particular phosphine desired. Particular difficulties often arise when mixed aryl-alkyl phosphines are desired.

The class of mixed aryl-alkyl phosphines is illustrated by the bis(diphenylphosphino)alkanes. Such bisphosphines have demonstrated and widespread utility as components of catalyst compositions which also include Group VIII metal compounds. One use of such catalyst compositions is in the production of linear alternating polymers of carbon monoxide and at least one ethylenically unsaturated hydrocarbon. These polymers have the repeating formula $-CO-(-A-)$ wherein A represents ethylenically unsaturated hydrocarbon polymerized through the ethylenic unsaturation. By way of further illustration, when the at least one ethylenically unsaturated hydrocarbon is ethylene, the linear alternating polymer is represented by the repeating formula $-CO-(-CH_2-CH_2-)$. Illustrative methods for the production of such polymers are disclosed in Published European Patent Applications 121,965 and 181,014. The catalyst compositions therein described include compositions formed from a compound of a Group VIII metal such as a palladium carboxylate, the anion of a strong non-hydrohalogenic acid and a bis(phenylphosphino)alkane. The bis(diphenylphosphino)alkanes were particularly useful, especially bis(diphenylphosphino)propane. For other modifications of the polymerization process, bis(substituted-phenylphosphino)alkanes have been found to be useful, particularly 1,3-bis[di(2-alkoxyphenyl)phosphino]-propane. Such a process is described and claimed in copending U.S. patent application Serial No. 930,468; filed Nov. 14, 1986

One method of producing bis(phenylphosphino)alkanes is shown by U.K. Patent Application 2,101,601. This process involves a multi-step process employing a phosphonium salt as an intermediatre. An alternate process for the production is shown by Chatt et al, *J. Chem. Soc. Dalton Trans.*, pp. 1131–1136 (1985). The Chatt et al process involves the use of a bis(dichlorophosphino)alkane, the production of which is said to require iron equipment which slowly degrades during reaction. A method described in copending U.S. patent application Serial No.07/175,021, filed Mar. 30, 1988 (Attorney's Docket No. T-0283) comprises reaction of a dihaloalkane and an alkali metal (di(alkoxyphenyl)phosphide produced by reaction of elemental alkali metal and the corresponding tri(alkoxyphenyl)phosphine. It would be of advantage to provide an alternate method for producing bis(alkoxyphenyl)phosphino alkanes.

SUMMARY OF THE INVENTION

This invention relates to a process for the production of bis(alkoxyphenyl)phosphine alkanes. More particularly it relates to a process for the production of 1,3-bis[di(2-alkoxyphenyl)phosphino]propane.

DESCRIPTION OF THE INVENTION

The process of the invention comprises a multi-step reaction for the production of 1,3-bis[di(2-alkoxyphenyl)phosphino)propane he first of which involves multiple reactions but reactions which are conducted without the necessity for isolation of chemical intermediates. An appropriately substituted 2-alkoxyphenyl Grignard reactant and phosphorus trihalide are contacted to produce a di(alkoxyphenyl)phosphorus halide which is converted to the di(alkoxyphenyl)phosphine by reaction with an alkali metal-containing hydride followed by hydrolysis. This phosphine is typically recovered and subsequently reacted with a 1,3-dihaloalkane to produce the bisphosphine.

The Grignard reactant employed in the process of the invention is a 2-alkoxyphenylmagnesium halide wherein the alkoxy is lower alkoxy of up to 4 carbon atoms inclusive, preferably methyl, and the halide moiety is chloride or bromide, preferably bromide. Such Grignard reactants are produced by conventional techniques from the corresponding 2-alkoxyphenyl halide and magnesium, typically in the presence of an ether or other polar solvent in which the Grignard reactant is soluble. For example, 2-methoxyphenyl bromide reacts with magnesium in tetrahydrofuran to produce 2-methoxyphenylmagnesium bromide. Reaction conditions and reactant ratios for this conversion are well known but typically involve ratios of moles of 2-alkoxyphenylhalide to gram-atoms of magnesium that are substantially 1:1 and a liquid phase reaction environment at a temperature that is dependent in part on the solvent employed but typically is no higher than about 50° C. and frequently is much lower, e.g., a temperature as low as about $-70°$ C. The reaction is conducted in an inert atmosphere, customarily a nitrogen atmosphere.

The Grignard reactant is employed without purification or isolation in the reaction with phosphorus trihalide which follows in the reaction sequence. This reaction is most easily accomplished by adding to the phosphorus trihalide, preferably phosphorus trichloride, the solution of Grignard reactant, also at a temperature of from about $-70°$ C. to about 50° C., and under an inert reaction atmosphere such as nitrogen. The molar ratio of the Grignard reactant to the phosphorus trichloride which is usefully employed is from about 3:2 to about 5:2 but preferably is substantially stoichiometric, e.g., about 2:1.

The resulting product is a di(2-alkoxyphenyl)phosphorus halide, for example, di(2-methoxyphenyl)phosphorus chloride, which is isolated by conventional techniques such as precipitation, extraction or distillation but which is preferably employed in situ in the succeeding reaction. This in situ reaction without purification is permitted by the selectivity to the di(alkoxyphenyl)phosphorus halide which selectivity is quite high with little or no production of (2-alkoxyphenyl)phosphorus dihalide or tri(2-alkoxyphenyl)phosphine.

The di(2-alkoxyphenyl)phosphorus halide is converted to the corresponding di(2-alkoxyphenyl)phosphine by reaction with a metal hydride followed by hydrolysis. The reaction with metal hydride is most easily conducted by adding the metal hydride to the solution in which the di(2-alkoxyphenyl)phosphorus halide is formed. The metal hydride is added to the solution and the mixture is maintained at reaction temperature until reaction has taken place.

The metal hydride employed as a reactant is a hydride of a strong metal but is preferably an alkali metal-containing hydride including alkali metal hydrides such as sodium hydride, lithium hydride and potassium hydride as well as mixed metal hydrides containing alkali metal moieties such as lithium aluminum hydride and sodium borohydride. The preferred alkali metal-containing hydride is lithium aluminum hydride. This reaction takes place over a wide range of reaction temperatures and suitable reaction temperatures are from about −70° C. to about 70° C.. A convenient reaction temperature is the reflux temperature of the reaction mixture. Suitable reaction pressures are those sufficient to maintain a non-gaseous phase reaction mixture. Subsequent to reaction of the di(2-alkoxyphenyl)-phosphorus halide and the alkali metal-containing hydride, the product mixture is hydrolyzed, preferably by contact with an excess of an aqueous solution of a strong electrolyte salt such as an ammonium salt. A saturated solution of ammonium chloride in water is a particularly effective hydrolysis media.

The resulting product is a di(2-alkoxyphenyl)phosphine which is isolated by conventional methods as described above. The secondary phosphine is produced in good yield, but the effective yield is even higher since the major by-product is the corresponding di(2-alkoxyphenyl)phosphine oxide which is able to be reduced by well known methods to improve the yield of the secondary phosphine or alternatively the phosphine oxide is recycled to an earlier reaction step to thereby promote the production of additional secondary phosphine.

The final conversion of the process of the invention, and the second process operation, is reaction of the di(2-alkoxyphenyl)phosphine and a 1,3-dihalopropane. Although chloro or bromo or mixtures are suitable halo substituents on the 1,3-halopropane reactant, the preferred 1,3-dihalopropane reactant is 1,3-dichloropropane. The secondary phosphine and the 1,3-dihalopropane are contacted in the presence of a strong base in a polar organic solvent. Suitable strong bases include the alkali metal hydroxides such as sodium hydroxide and potassium hydroxide. Also suitable, and generally preferred, is the strong base of unknown structure termed 'dimsyl sodium' which is produced by reaction of sodium hydride and dimethylsulfoxide. Largely because of this presence of strong base, the preferred reaction solvent for reaction of the secondary phosphine and the 1,3-dihalopropane is also dimethyl sulfoxide although other polar solvents including ethers and sulfones are suitable.

The di(2-alkoxyphenyl)phosphine and the 1,3-dihalopropane are contacted in a molar ratio of from about 1:1 to about 4:1 but preferably in a ratio of from about 1.5:1 to about 2.5:1. Reaction suitably takes place at a temperature from about 0° C. to about 70° C., preferably from about 10° C. to about 30° C., and at a pressure sufficient to maintain a non-gaseous reaction mixture. Subsequent to reaction, the 1,3-bis[di(2-alkoxyphenyl)-phosphino]-propane is recovered by conventional methods such as described above.

The bis(alkoxyphenyl)phosphino propane is useful as a ligand of transition metal catalyst compositions which are employed to catalyze a number of chemical transformations. One of the many examples of the use of such catalyst compositions is in the production of linear alternating polymers of carbon monoxide and at least one ethylenically unsaturated hydrocarbon, illustratively produced by the process of the above copending U.S. patent application Ser. No. 930,468, filed Nov. 14, 1986. The catalyst composition of this application comprises, inter alia, a palladium carboxylate such as palladium acetate, the anion of a strong non-hydrohalogenic acid such as trifluoroacetic acid or p-toluenesulfonic acid, and a bidentate phosphorus ligand.

The invention is further illustrated by the following Illustrative Embodiments which should not be construed as limiting.

ILLUSTRATIVE EMBODIMENT I

A Grignard reagent solution (2-methoxyphenylmagnesium bromide) was produced from 61.0g of 2-methoxyphenyl bromide and 9.5g magnesium in 350 ml of tetrahydrofuran. This solution was filtered through glass wool, cooled to −60° C. and, under nitrogen, dripped into a solution of 21.8g phosphorus trichloride in 400 ml tetrahydrofuran. After standing overnight at ambient temperature, the solution was cooled again to −60° C. and 2.2g of lithium aluminum hydride was added. The resulting solution was stirred for one hour at −60° C., warmed to room temperature and then heated to 50° C. and maintained at that temperature for three hours. The solution was then cooled to 0° C. and saturated ammonium chloride was added. The tetrahydrofuran layer was separated and concentrated by evaporation. Distillation of the product mixture thus obtained afforded 15.1g of di(2-methoxyphenyl)-phosphine, a 39% yield, b.pt 130° C. at 0.05 mm. The 15 g residue was principally the corresponding di(2-methoxyphenyl)phosphine oxide, from which additional di(2-methoxyphenyl)-phosphine could be obtained by reduction.

A solution of dimsyl sodium in dimethyl sulfoxide was produced from 0.65g sodium hydride and 15ml dimethyl sulfoxide. This solution was then added to 5.7g of di(2-methoxyphenyl)phosphine in 50ml of dimethyl sulfoxide. The resulting mixture was heated to 50° C. and 1.3g of 1,3-dichloropropane in 5 ml of dimethyl sulfoxide was added. The resulting mixture was heated to 50° C., maintained at that temperature for 3 hours and then cooled to room temperature. When 50 ml of water was added to the reaction mixture, a white precipitate was obtained. The precipitate was recovered by filtration, washed with water and recrystallized from ethanol. The product, 1,3-bis[di(2-methoxyphenyl)-phosphino]propane, 3.6g, 58% yield, was obtained in the form of white needles, m.pt. 149°–150° C.

ILLUSTRATIVE EMBODIMENT II

When the procedure of Illustrative Embodiment I is repeated in substantially the same manner, except that the first reaction sequence was conducted at room temperature and the lithium aluminum hydride solution was added to the di(2-methoxyphenyl)phosphine chloride solution, a good overall yield of the 1,3-bis[di(2-methoxyphenyl)phosphino]propane will be obtained.

What is claimed is:

1. A process for the production of 1,3-bis[di(2-alkoxyphenyl)phosphino]propane which comprises (1) reacting 2-alkoxyphenyl halide with magnesium, thereby producing the corresponding 2-alkoxyphenyl-magnesium halide; (2) reacting said 2-alkoxyphenylmagnesium halide with phosphorus trihalide, thereby producing the corresponding di(2-alkoxyphenyl)phosphorus halide; (3) producing from said di(2-alkoxyphenyl)phosphorus halide the corresponding di(2- alkoxyphenyl)phosphine by reaction with alkali metal-containing hydride followed by hydrolysis; and (4) reacting the di(2-alkoxyphenyl)phosphine with 1,3-dihalopropane in the presence of strong base, and recovering 1,3-bis[di(2-alkoxyphenyl)phosphino]propane from the resulting mixture.

2. The process of claim 1 wherein the 2-alkoxyphenyl halide is a 2-methoxyphenyl halide.

3. The process of claim 2 wherein the 2-methoxyphenyl halide is 2-methoxyphenyl bromide.

4. The process of claim 3 wherein the alkali metal-containing hydride is lithium aluminum hydride.

5. The process of claim 4 wherein the 1,3-dihalopropane is 1,3-dichloropropane.

6. The process of claim 1 wherein said hydrolysis in step (3) comprises contacting said di(2-alkoxyphenyl)-phosphine with a saturated solution of ammonium chloride in water.

7. The process of claim 1 wherein said 1,3-bis[di(2-alkoxyphenyl)-phosphino]propane is recovered in step (4) by filtration.

* * * * *